United States Patent [19]
Williams

[11] Patent Number: 5,827,322
[45] Date of Patent: Oct. 27, 1998

[54] SHAPE MEMORY LOCKING MECHANISM FOR INTRAVASCULAR STENTS

[75] Inventor: Michael S. Williams, Chapel Hill, N.C.

[73] Assignee: Advanced Cardiovascular Systems, Inc., Santa Clara, Calif.

[21] Appl. No.: 717,324

[22] Filed: Sep. 20, 1996

Related U.S. Application Data

[63] Continuation of Ser. No. 340,612, Nov. 16, 1994, abandoned.

[51] Int. Cl.$^6$ ................................................. A61M 29/00
[52] U.S. Cl. ................................ 606/198; 623/1; 623/12; 604/96
[58] Field of Search ............................... 606/1, 108, 191, 606/192, 194, 195, 198, 200; 623/1, 12

[56] References Cited

U.S. PATENT DOCUMENTS

| | | |
|---|---|---|
| Re. 31,474 | 12/1983 | Brook et al. . |
| 3,174,851 | 3/1965 | Buehler et al. . |
| 3,700,434 | 10/1972 | Abkowitz et al. . |
| 3,753,700 | 8/1973 | Harrison et al. . |
| 3,868,956 | 3/1975 | Alfidi et al. . |
| 3,913,444 | 10/1975 | Otte . |
| 3,989,552 | 11/1976 | Brook et al. . |
| 4,019,925 | 4/1977 | Nenno et al. . |
| 4,036,669 | 7/1977 | Brook et al. . |
| 4,144,057 | 3/1979 | Melton et al. . |
| 4,282,033 | 8/1981 | Goldstein et al. . |
| 4,304,613 | 12/1981 | Wang et al. . |
| 4,505,767 | 3/1985 | Quin . |
| 4,533,411 | 8/1985 | Melton . |
| 4,565,589 | 1/1986 | Harrison . |
| 4,631,094 | 12/1986 | Simpson et al. . |
| 4,654,092 | 3/1987 | Melton . |
| 4,665,906 | 5/1987 | Jervis . |
| 4,740,253 | 4/1988 | Simpson et al. . |
| 4,770,725 | 9/1988 | Simpson et al. . |
| 4,795,458 | 1/1989 | Regan . |
| 4,848,343 | 7/1989 | Wallsten et al. . |
| 4,894,100 | 1/1990 | Yamauchi et al. . |
| 4,919,177 | 4/1990 | Homma . |
| 4,935,068 | 6/1990 | Duerig . |
| 4,969,890 | 11/1990 | Sugita et al. . |
| 4,984,581 | 1/1991 | Stice . |
| 4,991,602 | 2/1991 | Amplatz et al. . |
| 5,026,441 | 6/1991 | Kim et al. . |
| 5,037,427 | 8/1991 | Harada et al. . |
| 5,067,957 | 11/1991 | Jervis . |
| 5,069,226 | 12/1991 | Yamauchi et al. . |
| 5,092,941 | 3/1992 | Miura . |
| 5,120,308 | 6/1992 | Hess . |
| 5,158,548 | 10/1992 | Lau . |
| 5,190,546 | 3/1993 | Jervis . |
| 5,197,978 | 3/1993 | Hess . |
| 5,219,358 | 6/1993 | Bendel et al. . |
| 5,231,989 | 8/1993 | Middleman et al. . |

(List continued on next page.)

FOREIGN PATENT DOCUMENTS

| | | |
|---|---|---|
| 0 554 082 | 8/1993 | European Pat. Off. . |
| 0 621 017 | 10/1994 | European Pat. Off. . |
| 0 621 017 A1 | 10/1994 | European Pat. Off. . |

OTHER PUBLICATIONS

Tominaga, et al., Effects of Design Geometry of Intravascular Endoprostheses on Stenosis Rate in Normal Rabbits, *American Heart Journal*, pp. 21–28, Jan. 1992.

Oku, et al., A Titanium–Nickel Alloy Intravascular Endoprosthesis In Vitro Studies, *Trans Am Soc Artif Intern Organs*, Vo. XXXIV, pp. 399–403, 1988.

*Primary Examiner*—William Lewis
*Attorney, Agent, or Firm*—Fulwider Patton Lee & Utecht, LLP

[57] ABSTRACT

An expandable intraluminal vascular graft is implanted in a coronary artery or other vessel to maintain the patency of the lumen. The vascular graft, commonly referred to as a stent, expands from a first diameter to a second diameter, and a plurality of teeth are moved in relation to a longitudinal slot to lock the stent in an expanded condition.

35 Claims, 5 Drawing Sheets

U.S. PATENT DOCUMENTS

| | | |
|---|---|---|
| 5,238,004 | 8/1993 | Sahatjian et al. . |
| 5,271,975 | 12/1993 | Solano . |
| 5,318,528 | 6/1994 | Heaven et al. . |
| 5,334,168 | 8/1994 | Hemmer . |
| 5,341,818 | 8/1994 | Abrams et al. . |
| 5,356,413 | 10/1994 | Martins et al. . |
| 5,365,943 | 11/1994 | Jansen . |
| 5,368,049 | 11/1994 | Raman et al. . |
| 5,372,599 | 12/1994 | Martins . |
| 5,408,932 | 4/1995 | Hesse et al. . |
| 5,409,015 | 4/1995 | Palermo . |
| 5,411,476 | 5/1995 | Abrams et al. . |
| 5,411,549 | 5/1995 | Peters . |
| 5,441,515 | 8/1995 | Khosravi et al. . |
| 5,443,500 | 8/1995 | Sigwart . |
| 5,480,383 | 1/1996 | Bagaoisan et al. . |
| 5,492,119 | 2/1996 | Abrams . |
| 5,505,735 | 4/1996 | Li . |
| 5,507,826 | 4/1996 | Besselink et al. . |
| 5,514,115 | 5/1996 | Frantzen et al. . |

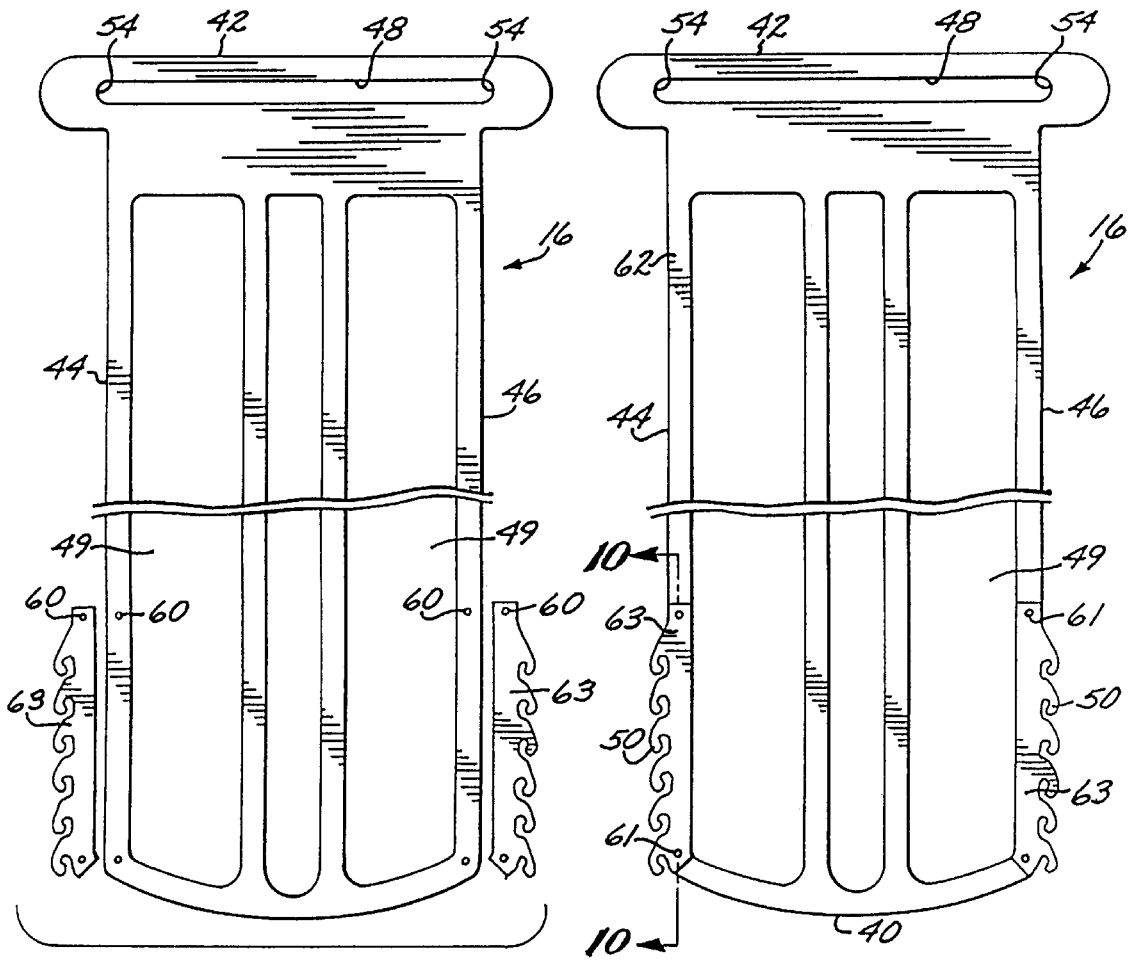
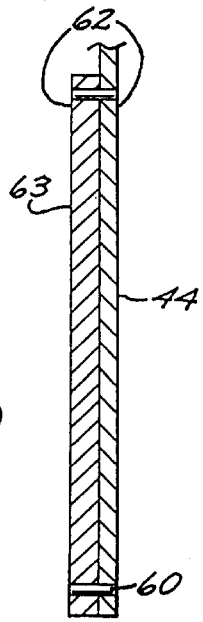

SHAPE MEMORY LOCKING MECHANISM FOR INTRAVASCULAR STENTS

This is a continuation of application Ser. No. 08/340,612, filed Nov. 16, 1994, now abandoned.

BACKGROUND OF THE INVENTION

1. Field of the Invention

The present invention generally relates to expandable endoprosthesis devices, in particular expandable intraluminal vascular grafts, generally called stents, adapted to be implanted in a body lumen, such as a coronary artery or other vessel to maintain the patency of the lumen. These devices are frequently used in the treatment of atherosclerotic stenosis in blood vessels especially after percutaneous transluminal coronary angioplasty (PTCA) procedures, with the intent to reduce the likelihood of restenosis of a blood vessel. Stents are also used to support a body lumen where a flap or dissection has occurred or in general where the lumen is weak. The present invention also relates to an expandable intraluminal vascular graft that can be used in essentially any body lumen.

2. Description of Related Art

In expandable stents that are delivered with expandable catheters, such as balloon catheters, the stents are positioned over the balloon portion of the catheter and are expanded from a reduced diameter to an enlarged diameter greater than or equal to the diameter of the arterial wall, by inflating the balloon. Stents of this type can be expanded to an enlarged diameter by deforming the stent, by engagement of the stent walls with respect to one another, and by one way engagement of the stent walls together with endothelial growth onto and over the stent. Other stents are self expanding, through the properties of the material constituting the stent or by design. Examples of intravascular stents can be found in U.S. Pat. No. 5,292,331 (Boneau); U.S. Pat. No. 4,776,337 (Palmaz); U.S. Pat. No. 4,580,568 (Gianturco); U.S. Pat. No. 4,856,516 (Hillstead); and U.S. Pat. No. 5,092,877 (Pinchuk), which are incorporated herein by reference in their entirety.

Current stent designs include a series of stents which are interconnected and utilize teeth on their outer edges to ratchet through a slot in order to achieve mechanical locking of a stent in a cylindrical form. Examples of such ratcheting stents can be found in co-pending application U.S. Ser. No. 08/052,410 and assigned to common assignee, Advanced Cardiovascular Systems, Inc. The ratcheting stent design of the prior art is generally made of 316L stainless steel, LPLA, DLPLA, or PCL polymers. If one is not careful, during the manufacturing process of rolling and during the deployment process in implanting the stent, it is possible that the teeth, because of the polymer material properties, may be deformed or damaged and thus affect stent-locking performance. Further, the ratcheting forces required to expand and deploy the stent can be higher than preferred because of the interference between the teeth and the locking slot. Also, the interference of the teeth with the locking slot may be somewhat offset and cause an uneven expansion of the individual rings of the stent.

Because the present invention is made from a shape-memory material, the interlocking teeth do not engage the slot until after expansion has occurred, thus eliminating some of the difficulties with the prior art devices.

SUMMARY OF THE INVENTION

The present invention is directed to an intravascular stent which is adapted to be inserted within a body lumen and designed to expand and lock in an enlarged diameter form. The stent of the present invention is designed to engage into the locked position after the stent has been expanded, by utilizing shape memory-retaining material in teeth which move when heated into engagement with a longitudinal slot. Thus, an intraluminal stent is formed from a substantially rectangular sheet having a longitudinal slot formed in one edge. A plurality of teeth are positioned along the edges of the sheet and intersect with said longitudinal slot in a belt buckle fashion. The stent is rolled onto a balloon portion of a catheter to form a cylindrical configuration and the stent is delivered within a body lumen for deployment. The balloon portion of the catheter is expanded which thereby expands the stent into engagement with the vascular wall of the body lumen. Thereafter, heat is applied to the stent and the teeth will move as a result of the heat so that the teeth engage and interlock with the longitudinal slot. The stent is then locked in an open position to hold the body lumen in an open position. The teeth can be made from any shape memory-retaining material such as nitinol (NiTi). Generally, NiTi as used in this invention is in the form of foil having either shape memory effect (SME) or super elasticity (SE).

Heat can be applied to the stent by several methods, one of which is a heated balloon. A saline solution that is heated is used to inflate the balloon and cause the teeth to heat and moving into locking engagement with the longitudinal slot as described above. Another method of heating the stent includes injecting heated saline into the body lumen after balloon expansion at the site of the implanted stent.

The present invention allows the stent to be expanded from a smaller diameter as it is rolled on the balloon to the larger expanded diameter for implanting in the diseased area without fear that the engaging teeth will be damaged, or cause the stent to deploy unevenly if one set of teeth engage while the other set does not. Further, deployment can be in a smoother and slower manner than with previous designs because the teeth are not ratcheting along the longitudinal slot as the stent is being expanded. It is only after the stent is expanded and heated, that the teeth engage the longitudinal slot.

The stent of the present invention also may be encapsulated by a polymer coating such that at least the locking mechanism components are coated. Thus, at least the teeth and the slot they engage are coated with a polymer. As is clear, however, other portions of the stent can be coated as well.

BRIEF DESCRIPTION OF THE DRAWINGS

FIG. 8 is a top view of an intraluminal stent wherein separate stent sections are mounted on the stent structure.

FIG. 9 is a top view of an intraluminal stent wherein separate stent sections each having a plurality of teeth in their closed position have been attached to the stent structure.

FIG. 10 is a cross-sectional view taken along lines 10—10 depicting the stent section attached to the stent body.

DETAILED DESCRIPTION OF THE PREFERRED EMBODIMENTS

During PTCA procedures it is common to use a dilatation catheter to expand a diseased area to open the patient's lumen so that blood freely flows. Despite the beneficial aspects of PTCA procedures and its widespread and accepted use, it has several drawbacks, including restenosis and perhaps acute thrombosis and sub-acute closure. This recurrent stenosis has been estimated to occur in seventeen to fifty percent of patients despite the initial PTCA procedure being successful. Restenosis is a complex and not fully understood biological response to injury of a vessel which results in chronic hyperplasia of the neointima. This neonintimal hyperplasia is activated by growth factors which are released in response to injury. Acute thrombosis is also a result of vascular injury and requires systemic antithrombotic drugs and possibly thrombolytics as well. This therapy can increase bleeding complications at the catheter insertion site and may result in a longer hospital stay. Sub-acute closure is a result of thrombosis, elastic recoil, and/or vessel dissection.

Several procedures have developed to combat restenosis and sub-acute or abrupt closure, one of which is the delivery and implanting of an intravascular stent. Stents are in their developmental stage at this point and are being used in clinical trials throughout the United States and are regularly implanted in patients in Europe and other countries. Generally speaking, the stents can take numerous forms, however, most common is a generally cylindrical hollow tube that holds open the vascular wall at the area that has been dilated by the dilatation catheter.

Figure 1:
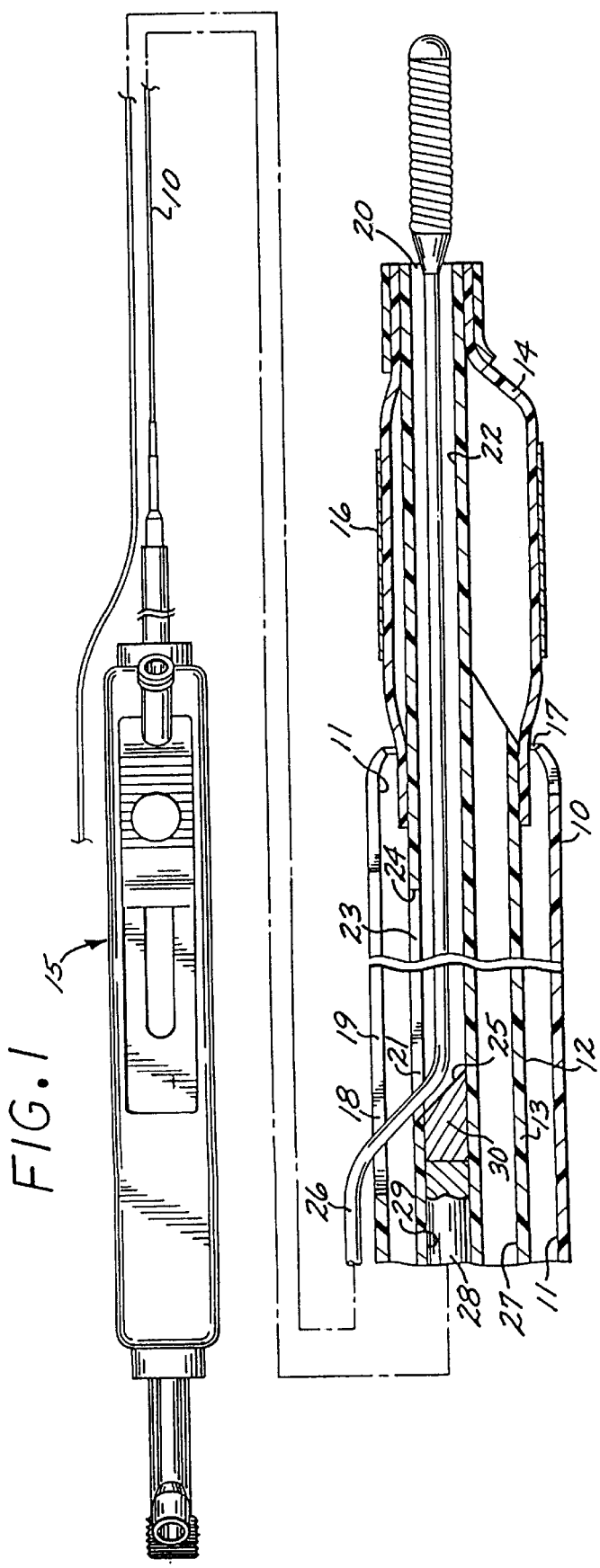
FIG. 1 depicts an intraluminal catheter having rapid exchange features for the purpose of delivering an intraluminal stent such as the ones shown in FIGS. 1 or 4.
Figure 2:
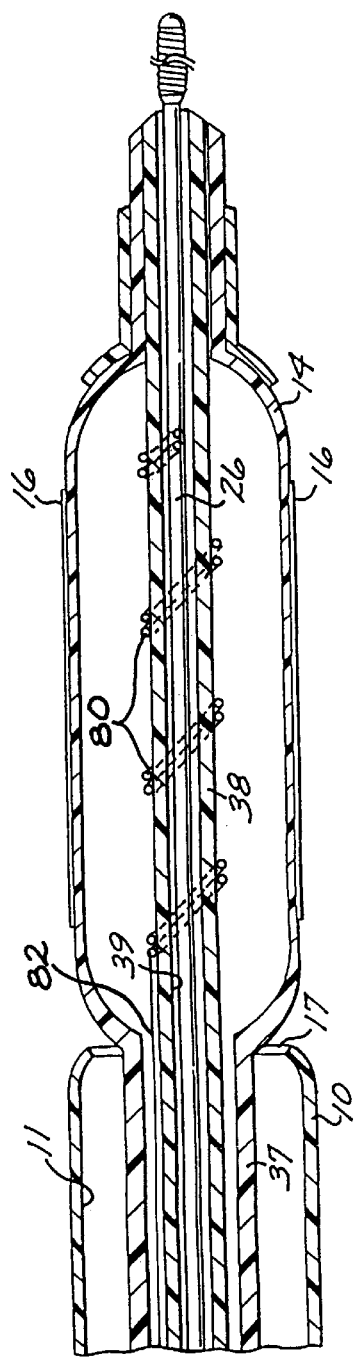
FIG. 2 is an over-the-wire-type intravascular catheter for delivering an intraluminal stent such as the ones depicted in FIGS. 1 or 4.

Generally speaking, stents are mounted on the balloon portion of catheter in a contracted state for intraluminal delivery to the injured or damaged area. The balloon is expanded and in turn expands the stent into engagement with the vascular wall. How the stent remains open is subject to the specific design. There are a wide range of catheter systems available to deploy these stents, two of which are depicted in FIGS. 1 and 2. In FIG. 1 a rapid exchange catheter system is depicted and in FIG. 2 an over-the-wire system is depicted. Each system incorporates a retractable sheath which protects the stent and the vessel wall as the stent is transported through the patient's vascular system. For purposes of the present invention, however, either system suffices and numerous other catheter systems would be appropriate, including perfusion catheters and dilatation catheters. Thus, FIGS. 1 and 2 illustrate a stent delivery system which embodies features of the invention.

Referring to FIG. 1, the delivery system includes a delivery sheath 10 which has an outer lumen 11 and an intravascular catheter 12 disposed within the outer lumen 11. The intravascular catheter has an elongated catheter body 13 and a balloon 14 on the distal portion of the catheter body. A manipulating device 15 is provided on the distal end of the delivery system which is employed to affect relative axial or longitudinal movement between the delivery sheath 10 and the intravascular catheter 12. An intravascular stent 16, which is to be delivered and implanted within a patient's body lumen, is mounted on the exterior of the balloon 14.

The delivery sheath 10 has a distal port 17 in its distal end which is in fluid communication with the outer lumen 11 and a proximal port 18 disposed proximally to the distal port. The distal portion of delivery sheath 10 tapers down in a spherical-like manner so that the cross-sectional area is somewhat less in the distal region than the cross-sectional area of the rest of the delivery sheath. A slit 19 extends from the proximal port 18 to a location just proximal to the distal port 17.

The intravascular catheter 12 has a distal port 20 and a proximal port 21 which are in fluid communication with a first inner lumen 22 extending within the distal portion of the catheter 12 and being adapted to slidably receive a guidewire therein. A slit 23 extends from the proximal port 21 to a location 24 proximal to the proximal end of balloon 14. The proximal end of the guidewire receiving first inner lumen 22 is provided with a ramp 25 to guide the proximal end of guidewire 26 out of the proximal port 21 of intravascular catheter 12 when the catheter is mounted onto the guidewire, as will be discussed hereinafter. A second, much longer inner lumen 27 is provided within the catheter body 13 to direct inflation fluid from the proximal end of the catheter body to the interior of balloon 14.

Proximal to the proximal port 21 in catheter body 13 is a stiffening member 28 which is disposed in third inner lumen 29 provided within catheter body 13. As shown in the drawings, third inner lumen 29 and first inner lumen 22 may be the same lumen with a plug 30 separating the two lumens. The ramp 25 is on the distal side of plug 30.

In a typical stent deployment, intravascular stent 16 will be implanted in a patient's vascular system at the diseased or injured area to provide sufficient blood flow through the vessel. The implanted stent 16 will aid in the prevention of restenosis, abrupt closure, and poor angiographic results. Typically, in these situations the distal end of a guidewire 26 (or other guiding member) extends across the damaged section of the artery while the proximal end of guidewire 26, extends out of the patient during the entire procedure and is inserted through the distal port 20 in the distal end of catheter 12 and advanced proximally through first inner lumen 22 until the proximal end of the guidewire impacts the ramp 25 and is thereby directed through the proximal port 21.

The intravascular catheter 12 is preferably positioned within outer lumen 11 of the delivery sheath 10 so that at least a significant portion of the proximal port 18 in the sheath is in alignment with the proximal port 21 of the intravascular catheter. In this manner, proximal advancement of the guidewire 26 through the inner lumen 22 will also direct the proximal end of the guidewire out the proximal port 18 in the delivery sheath. The proximal end of the guidewire 26 may then be manually held to maintain the position of the guidewire across the targeted area of deployment, while the catheter 12 and stent 16 are advanced over the guidewire and through the patient's vascular system. The advancement of the catheter system with stent 16 mounted thereon continues until the distal ends of the catheter and sheath extend adjacent to or across the targeted area of deployment. Next, the manipulator 15 on the proximal end of the delivery system is actuated to move sheath 10 proximally with respect to the catheter 12 and thereby expose stent 16 which is mounted on balloon 14. Thereafter, inflation fluid is directed under substantial pressure through inflation lumen 27 in the catheter body 13 to the interior of balloon 14, thereby expanding the balloon and simultaneously expanding stent 16 against the vessel wall of the patient. After balloon 14 is deflated, the delivery systems, both sheath 10 and catheter 12, are then removed from the patient along with guidewire 26, leaving the expanded stent 16 pressing against the vessel wall.

In another embodiment of the invention, as depicted in FIG. 2, an over-the-wire catheter system is employed to deliver the stent 16 within the patient's vasculature to the damaged area. A guidewire 26 is employed to cross a damaged area and locate the position within the patient so that the intravascular catheter 12 can reach the diseased or damaged area. As is typical in over-the-wire catheter systems, the intravascular catheter has an outer member 37 and an inner member 38 which are coaxially aligned. Inner member 38 has an inner lumen 39 which carries guidewire 26. The guidewire can move freely within inner lumen 39 in an axial direction. The intravascular catheter is slidably disposed within sheath 10 in inner lumen 11. Port 17 at the distal end of sheath 10 provides an opening for the catheter to extend.

The method of deploying stent 16 is similar to that described for the rapid exchange system described above and as depicted in FIG. 2. Generally, guidewire 26 is positioned at a location just past the targeted site of deployment and the catheter system is threaded over guidewire 26 so that balloon 14, along with stent 16 is positioned at the targeted area. Thereafter, balloon 14 is expanded radially outwardly to thereby expand and deploy stent 16 by forcibly expanding it into the vessel wall. Balloon 14 is then deflated and the catheter system 12 is withdrawn from the patient's vasculature leaving stent 16 securely implanted in the damaged or injured area.

Figures 3, 4:
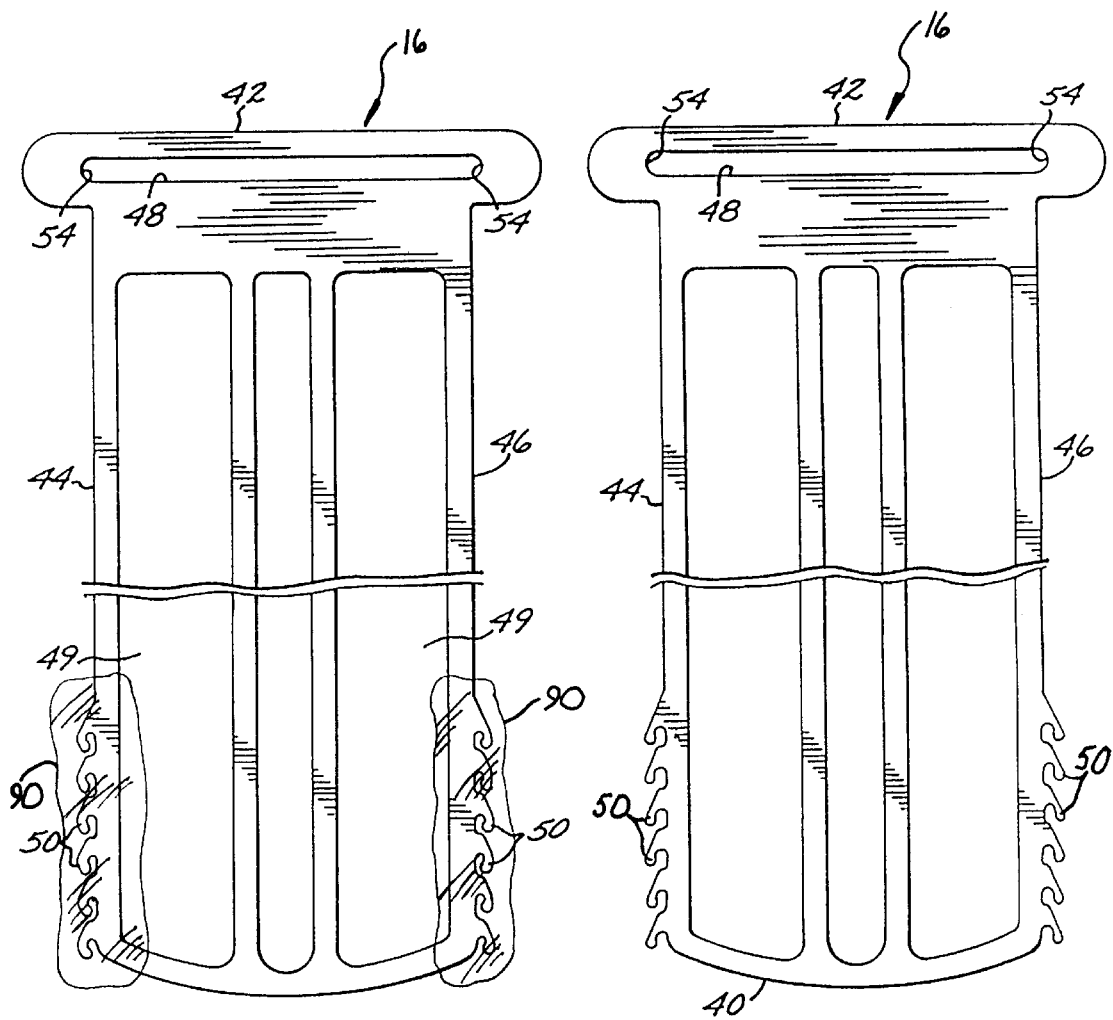
FIG. 3 is a top view of an intraluminal stent having a plurality of teeth which are locking mechanisms in their closed positions.
FIG. 4 is the intravascular stent of FIG. 1 wherein the plurality of teeth have moved outwardly into their locking position.

In keeping with the invention as depicted in FIGS. 3 and 4, intravascular stent 16 is depicted as a flat sheet which can be manufactured in numerous ways, including using a laser or chemical etchants. For example, a pattern is cut from a sheet of metal by using a $CO_2$ laser or a Nd:YAG laser to cut the pattern. Alternatively, a known etching process can be used to remove metal leaving the pattern depicted in FIGS. 3 or 4. Both laser and chemical etchant processes are described in U.S. Ser. No. 08/164,986, commonly assigned to Advanced Cardiovascular Systems, Inc., and which is incorporated herein by reference. Other known methods of making stent 16 include stamping and using an EDM process (electronic discharge machining).

The stent 16 depicted in FIG. 3 has a first edge 40 and a second edge 42, a third edge 44 and a fourth edge 46. It is desirable to have open spaces 49 cut within the stent body to allow more flexibility and to permit endothelial cell growth through the openings after the stent has been implanted and to allow for side branch flow and vessel wall oxygenation. Open spaces 49 can take any geometric shape as long as the expanded radial strength of stent 16 is maintained. A plurality of teeth 50 are formed along third edge 44 and fourth edge 46 and appear in a closed position. Teeth 50 are desirably made from a shape memory or superelastic material such as nitinol (NiTi) (see FIG. 8). The remainder of the stent 16 can be made of known materials such as stainless steel, tantalum, polymers, or composites of these materials. Further, closed teeth 50 can be attached to third edge 44 and fourth edge 46 by known means such as welding, brazing, staking, adhesives, or chemical bonding (see FIG. 8). It is also contemplated that all of stent 16 be made from a NiTi material, which would make the manufacturing process somewhat less complex.

In order to deploy stent 16 in a patient's vascular system, the stent must be capable of being rolled into a cylindrical configuration having a relatively low profile for delivery through the vascular system. Thereafter, and as described above, the balloon portion of a catheter will expand stent 16 to an enlarged diameter wherein it will press against the vessel wall and remain open. The present invention provides for a stent that is capable of expanding in a controlled manner and locking after the stent has been expanded.

Figure 4A:
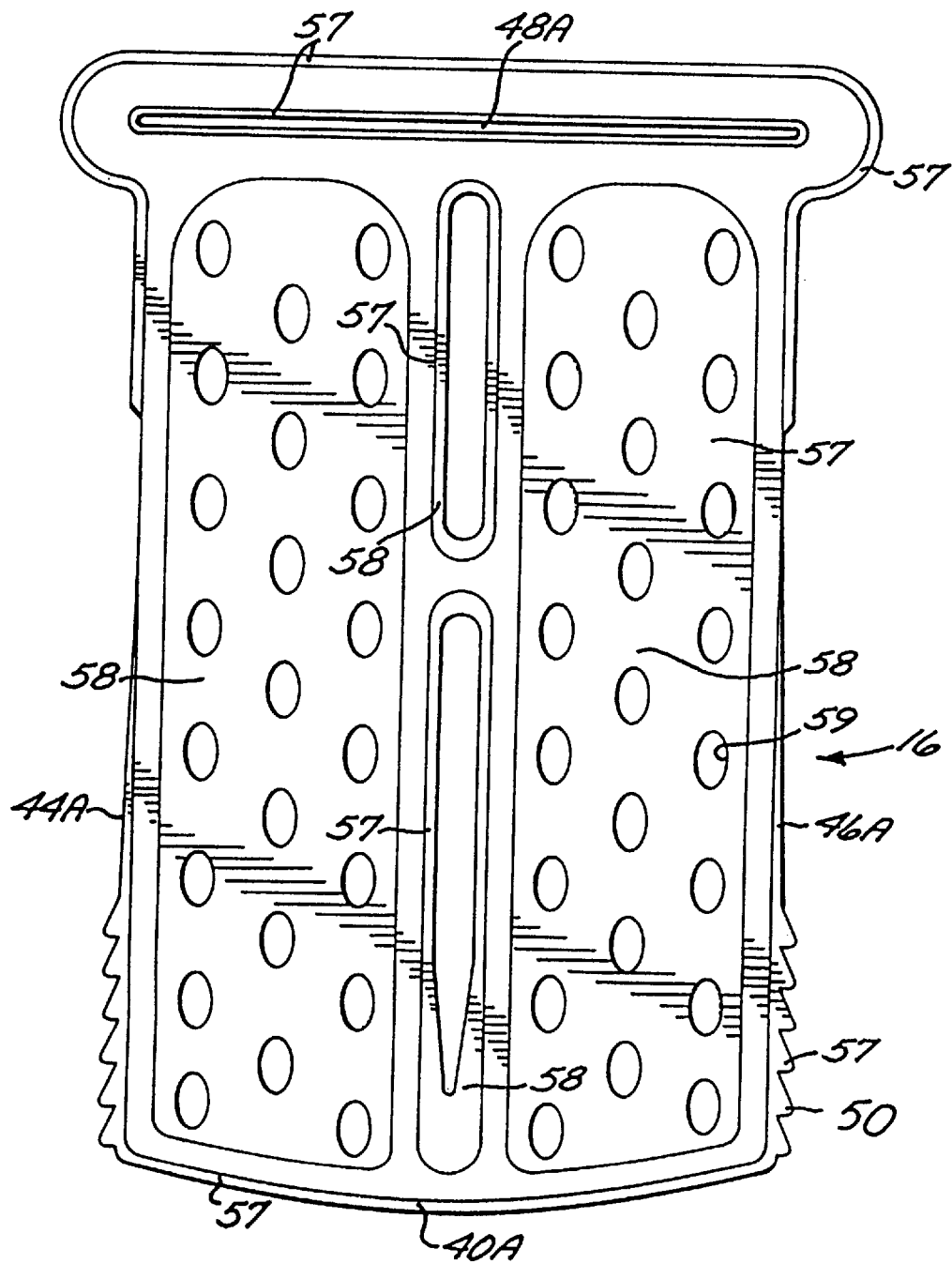
FIG. 4A is the intravascular stent of FIG. 4 wherein portions of the stent are encapsulated by a polymeric coating.

As is depicted in FIG. 4A, portions of the stent of the present invention can be encapsulated by a polymeric material. For example, stent 16 may have a polymeric coating 57 on open teeth 50, first edge 40A, third edge 44A, fourth edge 46A, and longitudinal slot 48A. Further, the polymeric coating 57 can fill openings 58. A plurality of holes 59 are formed in the polymeric coating 57 to provide more flexibility for stent 16 and provide more uniform expansion. The polymeric coating 57 can be comprised of poly-L-lactic acid (LPLA), poly-DL-lactic acid (DLPLA) or polycaprolactone (PCL) polymers, and the polymers can be loaded with a therapeutic drug which diffuses into the patient's body lumen at a controlled (predetermined) rate.

Figure 5:
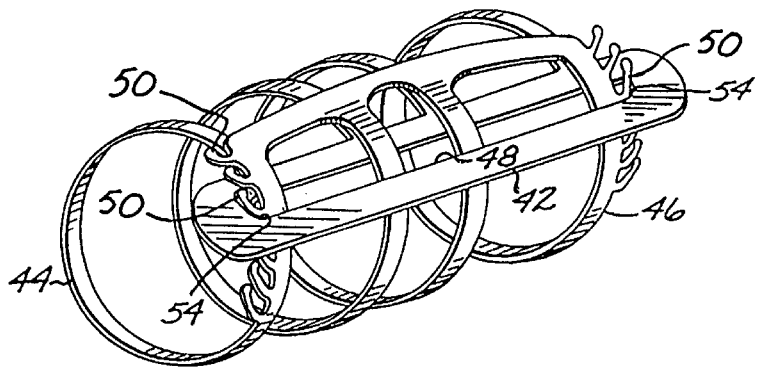
FIG. 5 is a perspective view of the intravascular stent of FIGS. 1 and 2 in which the stent has been rolled in a cylindrical configuration and the locking teeth have expanded into engagement with a slot.

In keeping with the invention, and as depicted in FIG. 5, stent 16 is rolled into a cylindrical configuration by inserting first edge 40 through longitudinal slot 48. Closed teeth 50 will not engage edges 54 of longitudinal slot 48, since teeth 50 are in their closed position and will simply slide past edges 54. In this manner, and as described above, the stent can be mounted on a balloon portion of a catheter and teeth 50 will not engage with edges 54 during either the rolling process or the expansion process as described further.

During delivery and implantation of stent 16, the catheter is used to position the balloon and stent in the diseased or injured area. Thereafter, the balloon is expanded thereby expanding stent 16 radially outwardly and into contact with the vessel wall. As closed teeth 50 move past edges 54 and slide through longitudinal slot 58, there is an even and uniform expansion since the teeth do not engage the edges. After fully expanding the stent, however, it is desirable to lock the stent in its fully open position.

Thus, it is desirable to move teeth 50 into an open position as shown by open teeth 50 in FIGS. 4 and 5. Teeth 56 move to their open position when they are heated to a specific temperature which is predetermined. For example, a heated saline solution or other fluid is injected into the balloon thereby heating stent 16 and teeth 50. Another method of heating includes injecting a heated saline solution into the body lumen at the site where stent 16 is implanted. Other means to heat stent 16 are available, such as using a thermal balloon device, using radio frequency waves to develop heat, or by induction heating. Such heating devices are well known in the art and are described, for example, in commonly owned U.S. Pat. No. 5,035,694 and U.S. Pat. No. 5,498,261, which are incorporated by reference herein in their entirety. For instance, balloon 14 as shown in FIG. 1 may include a thin electrically conductive layer that at least partially covers the outer surface of the balloon, or alternatively may be itself formed of conductive material. The balloon may be connected through wires running through the catheter body 13 to an exterior electrical power source that supplies electrical power to the conductive layer of the thermal balloon to generate heat. Alternatively, as shown in FIG. 2, a resistor element 80 such as a heating coil may be disposed within the interior of the balloon and connected to an external power source through a conductor 82. As will be appreciated by those skilled in the art, resistor element 80 may also be an induction element or an infrared heating element, similarly connected and disposed within balloon 14. The increase in temperature causes the teeth to move from their closed position to their open position and thereby engage with edges 54 of longitudinal slot 48. Once the teeth are engaged and locked, the balloon is deflated and the catheter system and balloon are withdrawn from the vascular system leaving the stent firmly implanted and in a fully open and locked position.

An advantage to the present invention is to permit a more uniform and low pressure expansion of stent 16 without concern of teeth 50 catching on the edges of the longitudinal slot and disrupting the deployment and expansion of the stent. Further, since teeth 50 are very small and susceptible to damage, having them closed during the expansion process minimizes the risk of damaging the teeth as they pass through the longitudinal slot.

In the preferred embodiment, the material considered best for the present invention is nitinol (NiTi). Shape memory of NiTi metallurgically represents a crystalline transition from the martensitic phase to the austenitic phase. The recovery or transition temperature may be altered by making minor variations in the composition of the metal and in processing the material. In developing the correct composition, biological temperature compatibility must be determined in order to select the correct transition temperature. In other words, when the stent is heated, it must not be so hot so that it is incompatible with the surrounding body tissue. Other shape, memory materials may also be utilized, such as, but not limited to, irradiated memory polymers such as autocrosslinkable high density polyethylene (HDPEX). As described above, the stent can be manufactured in several ways, including use of a laser or chemical etchants. Whichever process is used, the teeth will be annealed and formed so that they lay flush against the stent body in their closed position. The teeth are then cooled to room temperature so that they remain against the stent body until heated after the stent is fully expanded and implanted in the vessel wall.

Figure 6:
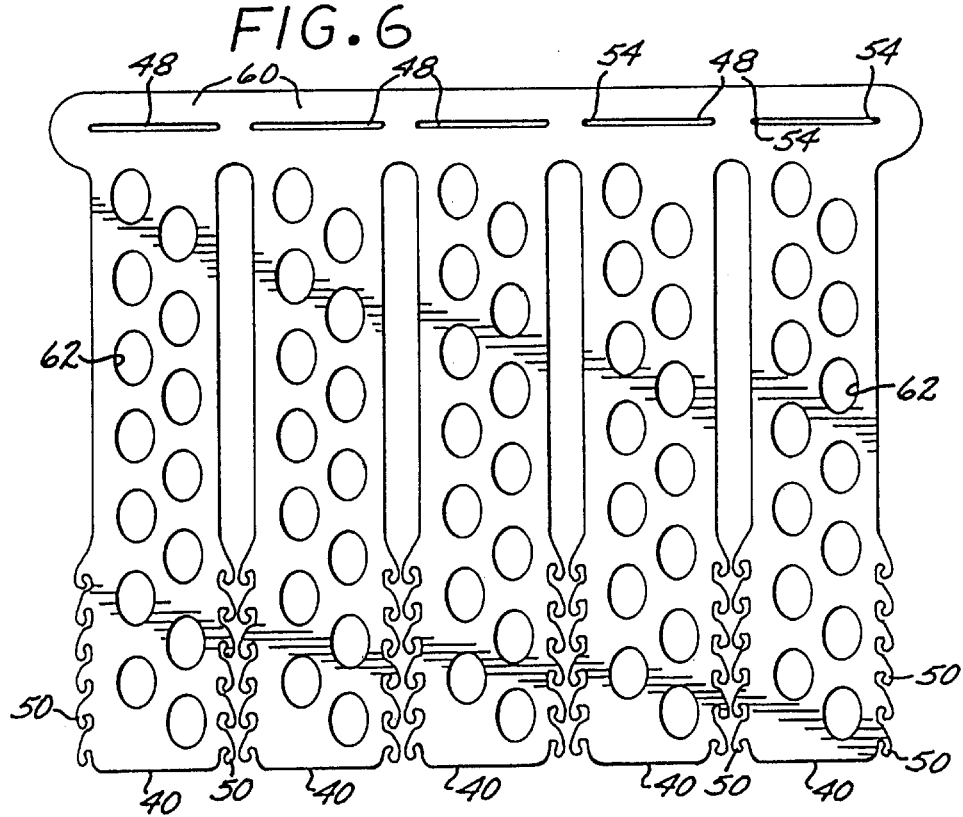
FIG. 6 is a top view of a plurality of interconnected intravascular stents with the plurality of teeth on each of the stent ends in their closed position.
Figure 7:
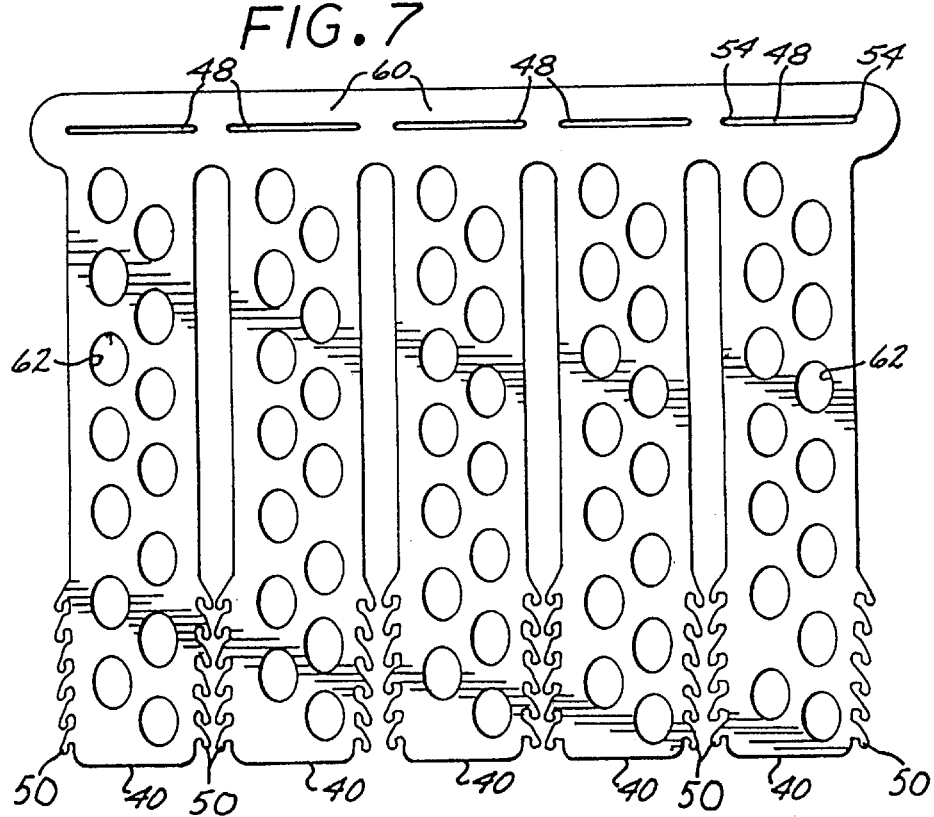
FIG. 7 depicts a top view of the intravascular stents of FIG. 4 wherein the plurality of teeth on each stent have opened outwardly for locking engagement.

While the invention has been depicted and described as a single stent having a cylindrical shape, a plurality of such stent strut components can be connected together to accomplish the same objective. As an example, as depicted in FIGS. 6 and 7, the plurality of stent strut components 60 are interconnected yet have the same basic features as the stent 16 as described in FIGS. 2–5. Open areas 62 can take any form as shown in FIGS. 6 and 7, and can be similar to the open areas 49 as depicted in FIG. 3. Again, open areas 62 provide greater flexibility to the stent as it is delivered on the balloon and subsequently expanded to its enlarged diameter. Open areas 62 also provide for cell growth from the patient's vessel wall into and over open areas so that a smooth cell structure eventually lines the inner wall of the stent to provide a restructured vessel. Open areas 62 also allow side branch flow and vessel wall oxygenation.

Because of its unique construction, stent strut components 60 can expand independently of one another and are flexible so that the stent can be implanted on a curved section of a patient's vasculature. As described above, first edge 40 is inserted through longitudinal slot 48 respectively for each of the stent strut components 60 depicted in FIG. 6. Further, closed teeth 50 are in their closed position and will not engage edges 54 of the longitudinal slot so that rolling and expansion can take place uniformly and without fear of damaging the teeth. Further as described above, after stent strut components 60 are expanded to an enlarged configuration, the teeth are moved to their open position as depicted by open teeth 50 in FIG. 7. Open teeth 50 will engage edges 54 of longitudinal slot 48 thereby locking stent strut components 60 in their fully open and expanded position.

There are generally two methods by which NiTi may be used with the present invention. First, an NiTi foil with SME (shape memory effect) is heat treated at approximately 500° C. The teeth are mechanically deformed into the closed position so that they remain closed until after the stent has been expanded and its temperature raised to a predetermined level. For example, after the stent has been expanded and deployed in the vessel wall, 45° C. heat is applied and the teeth will return to their open position and be locked into engagement with the longitudinal slot as described above. The application of 45° C. of heat is compatible with most applications in the human body, but it is not to be limited to this temperature as higher or lower temperatures are contemplated without departing from the invention.

A second method includes providing an NiTi foil having SE properties (super elastic properties) wherein the material is non-malleable and is heat treated to approximately 500° C. In this application, as illustrated in FIG. 3, the teeth are deformed and set into a very hydrophilic structure 90 such as hydrogel, glucose, acetate, starch, agar, or similar material. Once the stent is deployed and expanded in the vessel wall, the teeth will move to their open position as the hydrophilic structure is dissolved. Thus, the teeth will move to engage with the longitudinal slot thereby locking the stent in its fully open and expanded condition at the injured or diseased area.

In another embodiment of the invention, as depicted in FIGS. 8–10, the teeth portion which engage the longitudinal slot are shown as a separate add on section to the main stent. Thus, stent 16 has several alignment holes 60 that correspond to alignment holes 60 in teeth sections 63. The teeth sections 63 will overlay stent 16 and are aligned thereon using a pin or other alignment tool by inserting through the alignment hole 60. Teeth sections 63 are attached to stent 60 by any conventional means such as welding, brazing, adhesives, and the like. Either before or after teeth sections 63 are attached to stent 16, the entire structure is laminated with a thin polymer coating which allows for local delivery of drugs loaded in the polymer. Teeth sections 63 can be formed from a nitinol or other shape memory material such as that described above, while stent 16 can be made from any of the materials referred to above such as stainless steel, tantalum, polymers, NiTi, and the like. In use, stent 16 is deployed and implanted in the same manner described above for the other embodiments disclosed. Since teeth 50 are made from nitinol they will expand upon application of heat and engage longitudinal slot 48 in the same manner described above for the other embodiments. The thickness of stent 16 and teeth sections 63 can vary depending upon the application, however, they should be as thin as possible in order to provide a low profile for transport through the patient's vascular system, yet be thick enough to maintain structural integrity when the stent is fully expanded.

Any of the aforementioned embodiments can be laminated according to the following process. The stent, comprised of a NiTi foil having either SME or SE properties, is lased or etched into a specific configuration and thereafter heat treated in its flat condition at approximately 500° C.

The structure is laminated with a polymer or similar substance at approximately 190° C. The polymer laminate is ideally loaded with a therapeutic drug and will allow for localized drug delivery. The resulting structure can be lased again to refine the configuration, such as cutting the teeth or cutting various apertures so that the stent is more amenable to its biological environment. The laminate coating is then removed from the teeth so that the NiTi metal is exposed. The teeth are then collapsed and the stent is rolled into a cylindrical configuration onto the balloon portion of a catheter for intraluminal delivery. The manufacturing processes as described herein can vary, including temperatures and types and combinations of various materials. The foregoing methods of manufacture are described for example purposes only and are not meant to be limiting of the invention.

The dimensions of the intravascular catheter described herein will generally follow the dimensions of intravascular catheters used in angioplasty procedures in the same arterial location. Typically, the length of a catheter for use in the coronary arteries is about 150 cm, the outer diameter of the catheter shaft is about 0.035 inch (0.89 mm), the length of the balloon is typically about 2 cm, and the inflated diameter is approximately 1 to about 8 mm.

The materials of construction may be selected from those used in conventional balloon angioplasty catheters, such as those described in the patent incorporated herein by reference. The delivery sheath will generally be slightly shorter than the intravascular catheter, e.g., by about the length of the manipulating device 15, with an inner diameter large enough to accommodate the intravascular catheter and to allow the catheter free longitudinal movement therein. The sheath and the catheter shaft can be made of conventional polyethylene tubing, or any other material as described in the catheter patents incorporated herein by reference.

What is claimed is:

1. An intraluminal stent assembly which is implanted in a body lumen, comprising:
    an intraluminal stent formed from a substantially flat sheet and having a first edge and a second edge;
    a longitudinal slot in said first edge; and
    a plurality of teeth positioned along a third edge and a fourth edge of said stent for interlocking engagement with said longitudinal slot, said plurality of teeth made from a shape memory-retaining material or a superelastic material so that said stent can be rolled into a cylindrical configuration and when expanded to an enlarged diameter said plurality of teeth interlock with said longitudinal slot.

2. The stent assembly of claim 1, wherein said plurality of teeth move in response to a change in temperature so that said teeth engage with said longitudinal slot thereby locking said stent in an expanded cylindrical form.

3. The stent assembly of claim 1, wherein said plurality of teeth respond to a heated fluid to move into locking engagement with said longitudinal slot.

4. The stent assembly of claim 2, further comprising a catheter having a thermal balloon portion to heat the stent and thereby cause said plurality of teeth to move into engagement and interlock with said longitudinal slot.

5. The stent assembly of claim 2, further comprising a heating element to apply infrared heating to said stent, thereby causing said plurality of teeth to move into locking engagement.

6. The stent assembly of claim 2, further comprising a heating element to apply induction heating to said stent, thereby causing said plurality of teeth to move into locking engagement.

7. The stent assembly of claim 2, further comprising a catheter having resistor elements for providing heat to said stent, thereby causing said plurality of teeth to move into locking engagement with said longitudinal slot.

8. The stent assembly of claim 2, further comprising a catheter to inject a heated fluid into the patient's body lumen adjacent said stent, thereby heating said stent and causing said plurality of teeth to move into locking engagement with said longitudinal slot.

9. The stent assembly for the intraluminal stent of claim 8, wherein said intraluminal stent is formed from a material taken from the group of materials including nickel-titanium alloy, tantalum, polymers, and stainless steel, or any composite of said group of materials.

10. The stent assembly for the intraluminal stent of claim 1, wherein said plurality of teeth are formed from a nickel-titanium alloy.

11. The stent assembly for the intraluminal stent of claim 1, wherein said intraluminal stent is mounted on a balloon portion of a catheter and delivered intraluminally to a diseased area so that said balloon portion can expand and thereby expand said stent at the diseased area.

12. The stent assembly for the intraluminal stent of claim 1, wherein at least a portion of said stent is encapsulated by a polymeric coating.

13. The stent assembly for the intraluminal stent of claim 12, wherein said polymeric coating is made from a polymeric composition taken from the group of materials poly-L-lactic acid (LPLA), poly-DL-lactic acid (DLPLA), or polycaprolactone (PCL).

14. The stent assembly for the intraluminal stent of claim 13, wherein said polymeric coating is loaded with a therapeutic drug.

15. An intraluminal stent which is implanted in a body lumen comprising:
    a plurality of flat sheets interconnected together and each having a first edge and a second edge;
    a longitudinal slot formed in said first edge of each of said flat sheets; and
    a plurality of teeth positioned along a third edge and a fourth edge of each of said flat sheets for interlocking engagement with said longitudinal slot, said plurality of teeth made from shape memory-retaining materials so that said sheets can be rolled into a cylindrical configuration and when expanded to an enlarged diameter said plurality of teeth interlock with each of said corresponding longitudinal slots.

16. The stent of claim 15, wherein said plurality of teeth move in response to a change in temperature so that said teeth engage with said longitudinal slot thereby locking said stent in an expanded cylindrical form.

17. The stent of claim 15, wherein at least a portion of said intraluminal stent is made from a nickel-titanium alloy.

18. The stent of claim 15, wherein said plurality of teeth move into engagement with said longitudinal slots in response to heating applied to said plurality of teeth to a temperature sufficient to cause said teeth to move into locking engagement with said longitudinal slots.

19. An intraluminal stent which is implanted in a body lumen comprising:
    a substantially flat sheet having a first edge and a second edge;
    a longitudinal slot formed in said first edge; and
    a plurality of teeth positioned along a third edge and fourth edge of said sheet for interlocking engagement with said longitudinal slot, said plurality of teeth made from a super elastic material so that said sheet can be rolled into a cylindrical configuration and when expanded to a large diameter said plurality of teeth interlock with said longitudinal slot.

20. The stent of claim 19, wherein said plurality of teeth are set into a hydrophilic structure which will dissolve after said intraluminal stent has been implanted in a body lumen, thereby allowing said plurality of teeth to move into locking engagement with said longitudinal slot.

21. The stent of claim 20, wherein said hydrophilic material is taken from the group of materials including hydrogel, glucose, acetate, agar, and starch.

22. A locking mechanism for a substantially cylindrical stent formed from a substantially flat sheet having a first, second, third and fourth edge and including a longitudinal slot formed in the first edge for receiving the second edge, comprising:

a plurality of teeth positioned along the third and fourth edge of the stent, said teeth being movable between a closed position and an open position wherein said teeth remain substantially non-engaged within the longitudinal slot when in the closed position and in interlocking engagement within the longitudinal slot when in the open position, said plurality of teeth being formed from a shape memory alloy, whereby said plurality of teeth move between the closed and open positions by subjecting said teeth to a temperature change.

23. The locking mechanism according to claim 22, wherein said plurality of teeth are formed from a nickel-titanium alloy.

24. The locking mechanism according to claim 22, wherein the intraluminal stent is formed from a material taken from the group of materials including nickel-titanium alloy and irradiated memory polymers.

25. A locking mechanism for a substantially cylindrical stent implantable in a body lumen and formed from a substantially flat sheet having a first, second, third and fourth edge and including a longitudinal slot formed in the first edge for receiving the second edge, comprising:

a plurality of teeth positioned along the third and fourth edge of the stent, the teeth being movable between a closed position and an open position, the teeth remaining substantially non-engaged within the longitudinal slot when in the closed position and in interlocking engagement within the longitudinal slot when in the open position;

the plurality of teeth being formed from a super elastic alloy; and means for restraining the plurality of teeth in a deformed, closed conditioned thereby inducing a stress in the plurality of teeth.

26. The locking mechanism of claim 25, wherein the plurality of teeth are formed from the super elastic alloy of nickel-titanium.

27. The locking mechanism of claim 26, wherein the nickel-titanium is non-malleable and is heat treated to approximately 500° C.

28. The locking mechanism of claim 25, wherein the means for restraining the plurality of teeth in the deformed, closed condition to induce a stress in the teeth includes setting the plurality of teeth in a hydrophilic material.

29. The locking mechanism of claim 28, wherein the hydrophilic material is taken from the group of materials including hydrogels, glucose, acetates, starches, and agar.

30. A method for locking a stent in a substantially cylindrical condition in a body lumen, the method comprising:

providing a stent having a first edge, a second edge, a third edge, and fourth edge, the first edge including a longitudinal slot configured for receiving the second edge therethrough;

providing a plurality of teeth along the third edge and the fourth edge;

moving the plurality of teeth from a substantially non-engaging relationship with the longitudinal slot into an interlocking engagement with the longitudinal slot.

31. The method according to claim 30, wherein the providing-a-plurality-of-teeth step includes providing a plurality of teeth formed from a nickel-titanium alloy.

32. The method according to claim 31, wherein the moving-the-plurality-of-teeth step includes heating the nickel-titanium alloy to a temperature of about 45° C. so that the nickel-titanium alloy transforms from a martensitic state to a stable austenitic state and in the process the plurality of teeth move into interlocking engagement with the longitudinal slot.

33. The method according to claim 31, wherein the moving-the-plurality-of-teeth step includes inducing a stress in the teeth when in a closed, non-engaging relationship with the longitudinal slot, and removing the stress from the teeth whereby the teeth will move into the interlocking relationship with the longitudinal slot.

34. The method according to claim 33, wherein the inducing-stress-in-the-teeth step further includes setting the teeth in a hydrophilic material so the teeth remain in a closed, non-engaging position relative to the longitudinal slot.

35. The method according to claim 34, wherein the hydrophilic material dissolves upon contact with the blood, thereby relieving the stress in the teeth so that the teeth move into interlocking engagement with the longitudinal slot.

* * * * *

UNITED STATES PATENT AND TRADEMARK OFFICE
CERTIFICATE OF CORRECTION

PATENT NO. : 5,827,322
DATED : Oct. 27, 1998
INVENTOR(S) : Michael S. Williams

It is certified that error appears in the above-identified patent and that said Letters Patent is hereby corrected as shown below:

Column 10, claims 9,10,11,12,13 & 14, lines 10,15,18,23,26 & 31 respectively. after "stent" first occurrence, delete "assembly", and "stent" second occurrence, add --assembly--.

Signed and Sealed this

Twenty-third Day of March, 1999

Attest:

Attesting Officer

Q. TODD DICKINSON

Acting Commissioner of Patents and Trademarks